(12) United States Patent
Hosaka et al.

(10) Patent No.: US 8,177,710 B1
(45) Date of Patent: May 15, 2012

(54) ENDOSCOPIC DEVICE

(75) Inventors: Yoichi Hosaka, Iruma (JP); Yoshihisa Ishikawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/196,468

(22) Filed: Aug. 2, 2011

(51) Int. Cl.
*A61B 1/00* (2006.01)

(52) U.S. Cl. ........................................ 600/131; 600/146

(58) Field of Classification Search .................. 600/131, 600/197
See application file for complete search history.

(56) References Cited

U.S. PATENT DOCUMENTS

| | | | |
|---|---|---|---|
| 4,742,819 A * | 5/1988 | George | 600/109 |
| 5,183,031 A * | 2/1993 | Rossoff | 600/131 |
| D358,471 S | 5/1995 | Cope et al. | |
| 5,785,644 A * | 7/1998 | Grabover et al. | 600/131 |
| 6,315,712 B1 * | 11/2001 | Rovegno | 600/109 |
| 6,432,046 B1 * | 8/2002 | Yarush et al. | 600/179 |
| 6,752,758 B2 | 6/2004 | Motoki et al. | |
| 7,074,182 B2 * | 7/2006 | Rovegno | 600/131 |
| 7,179,223 B2 * | 2/2007 | Motoki et al. | 600/131 |
| 7,214,183 B2 * | 5/2007 | Miyake | 600/131 |
| 7,679,041 B2 | 3/2010 | Lia | |
| 7,956,888 B2 * | 6/2011 | Karpen | 348/85 |
| 2004/0054254 A1 | 3/2004 | Miyake | |
| 2007/0106117 A1 * | 5/2007 | Yokota | 600/120 |
| 2007/0249904 A1 * | 10/2007 | Amano et al. | 600/131 |
| 2007/0270647 A1 * | 11/2007 | Nahen et al. | 600/131 |
| 2008/0009677 A1 | 1/2008 | Shoroji et al. | |

FOREIGN PATENT DOCUMENTS

| | | |
|---|---|---|
| JP | 2004-109222 A | 4/2004 |
| JP | 2005-131161 A | 5/2005 |
| JP | 2009-189685 A | 8/2009 |

* cited by examiner

*Primary Examiner* — Matthew J Kasztejna

(74) *Attorney, Agent, or Firm* — Holtz, Holtz, Goodman & Chick, PC

(57) ABSTRACT

An endoscope includes an insert portion, a display portion, a manipulation portion, a casing which houses the display portion and the manipulation portion at a front side, and to which the insert portion is connected at a back side, and a battery. The casing has an upper portion in which the display portion is housed and a lower portion in which the manipulation portion is housed. The insert portion is connected to the lower portion and extends from the lower portion in a first direction. And a line connecting a center of gravity of the battery and a center of gravity of the casing while the battery is housed in the casing extends in a second direction that intersects the first direction at an angle.

1 Claim, 16 Drawing Sheets

ENDOSCOPIC DEVICE

BACKGROUND OF THE INVENTION

1. Technical Field

The present invention relates to an endoscopic device, and more particularly, to an endoscopic device in which an operation unit flexing an insertion section and a display unit displaying an image acquired by the insertion section are built in a single chassis.

2. Description of the Related Art

An endoscopic device having an image capturing mechanism at a distal end of a long insertion section has been widely used to observe a sample located at an end of a thin and long insertion channel or to observe the inside of a sample.

Recently, an improvement in which a display unit displaying an image acquired from the insertion section and an operation unit flexing the insertion section are received in a single chassis so as to facilitate the carrying and operation has been studied as an improvement of the endoscopic device.

Japanese Unexamined Patent Application, First Publication No. 2004-109222 discloses an endoscopic device in which a display unit and an operation unit are received in a common chassis. In the endoscopic device, a monitor unit is disposed at one end of the chassis and a substantially rod-shaped grip is formed at the other end. An operation unit including a joystick is disposed between the grip and the monitor unit. A user operates the joystick with a thumb in a state where he or she holds the rod-shaped grip at the time of operating the joystick.

SUMMARY OF THE INVENTION

According to one aspect of the invention, an endoscope includes a long flexible insert portion which has an imaging device on a tip thereof, a display portion which displays an image obtained by the imaging device, a manipulation portion for bending the insert portion, a casing which houses the display portion and the manipulation portion at a front side, and to which the insert portion is connected at a back side, and a battery which supplies electricity to the display portion. The casing has an upper portion in which the display portion is housed and a lower portion in which the manipulation portion is housed. The insert portion is connected to the lower portion and extends from the lower portion in a first direction. And a line connecting a center of gravity of the battery and a center of gravity of the casing while the battery is housed in the casing extends in a second direction that intersects the first direction at an angle.

DETAILED DESCRIPTION

Figure 1:
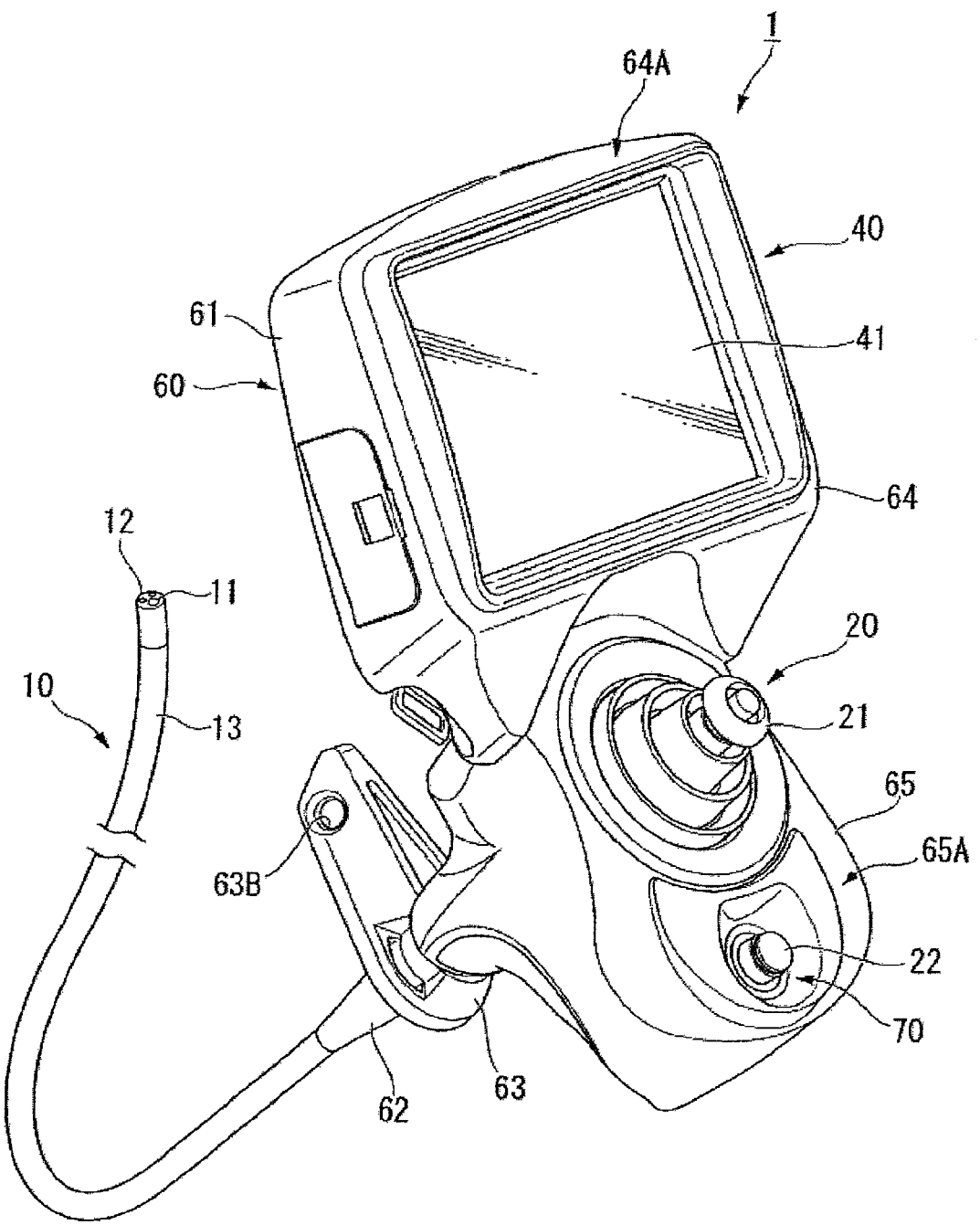
FIG. 1 is a perspective view illustrating the entire appearance of an endoscopic device according to an embodiment of the invention.

An endoscopic device according to an embodiment of the invention will be described with reference to FIGS. 1 to 11. The endoscopic device 1 according to this embodiment is used to observe a sample located at an end of a long and thin insertion channel or to observe the inside of the sample. As shown in FIG. 1, the endoscopic device 1 includes a long insertion section 10, an operation unit 20 flexing the insertion section 10, a display unit 40 displaying an image acquired from the insertion section 10, and a chassis unit 60 having a chassis 61 receiving the operation unit 20 and the display unit 40.

The insertion section 10 has a known configuration including an observation optical system 11, an illumination mechanism 12 such as an LED, and an image capturing mechanism such as a CCD not shown at a distal end thereof, and can acquire an image such as a still image or a moving image of a sample located in front of the distal end. The insertion section 10 also includes a known flexible portion 13 in which plural joint blocks or curved blocks (hereinafter, generally referred to as "joint blocks and the like") not shown are arranged and connected in the axis line direction and can be flexed in four directions in which it goes away from a central axis line thereof in two axes intersecting the central axis line. Operation members such as four wires corresponding to the four directions are connected to the joint block and the like closest to the distal end out of the plural joint blocks and the like. The operation members extend to the inside of the chassis unit 60 via the joint blocks and the like and are connected to the operation unit 20.

The operation unit 20 includes a first joystick (operation stick) 21 operating the flexible portion 13, a second joystick 22 operating a cursor displayed on the display unit 40, and a flexing mechanism being operated with the first joystick 21.

Figure 2:
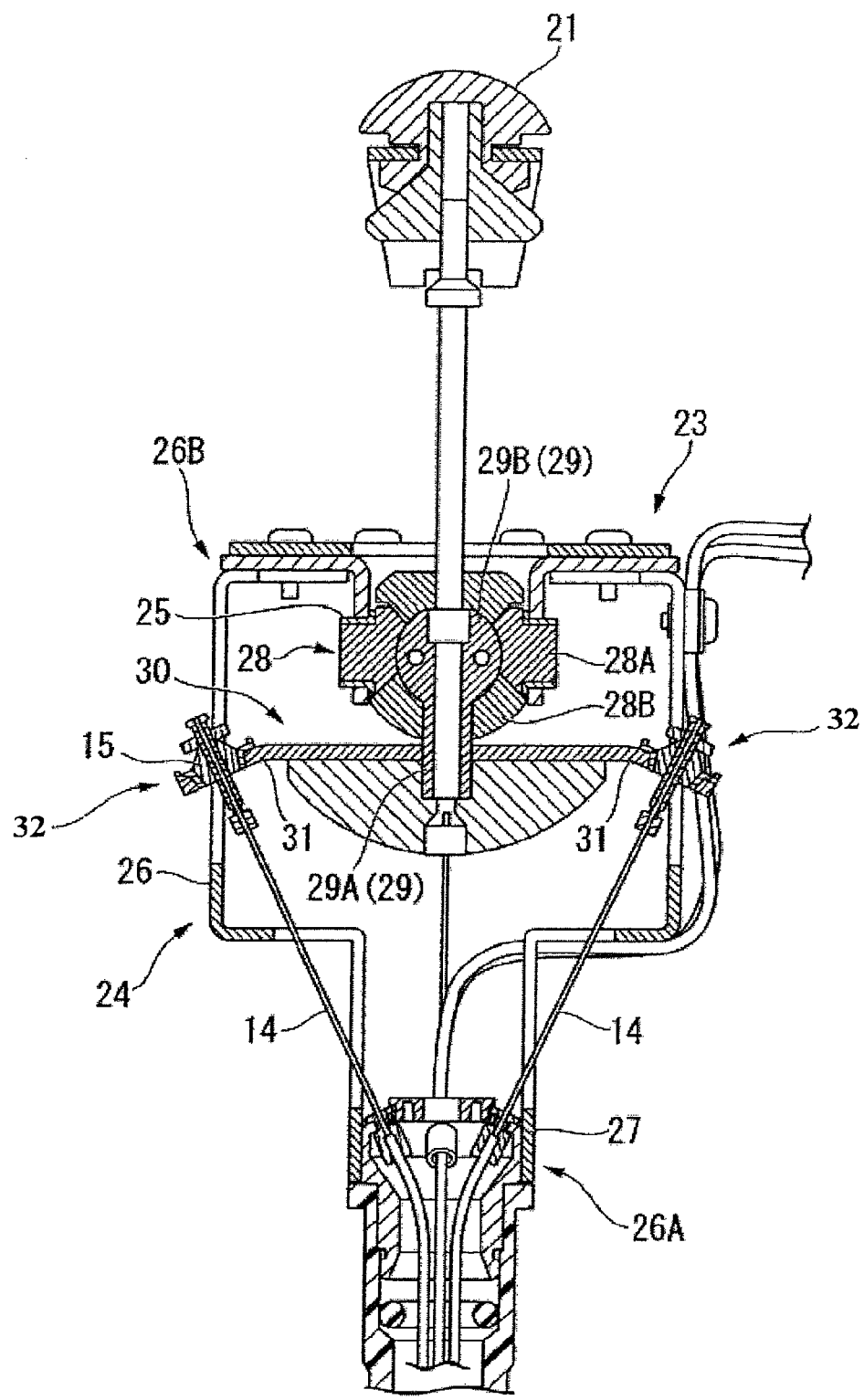
FIG. 2 is a diagram illustrating a first joystick and an operation mechanism of the endoscopic device.

FIG. 2 is a diagram illustrating the first joystick 21 and the flexing mechanism 23.

The flexing mechanism 23 includes a frame 24 and a rocking member 25 attached to the frame 24. The frame 24 is formed of a material such as metal having predetermined rigidity, and includes a rocking member receiving portion 26 to which the rocking member is attached and a guide portion 27 extending from the rocking member receiving portion 26.

The rocking member 25 includes a first member 28 rotatably attached to the frame 24, a second member 29 rotatably attached to the first member 28, and an operation member fixing portion 30 attached to the second member 29.

The first member 28 is formed of a material such as metal or resin and includes a rotation shaft portion 28A. The first member 28 is attached to a second end portion 26B opposite to a first end portion 26A from which the guide portion 27 extends in the rocking member receiving portion 26 so as to rotate in a predetermined range about the axis line of the rotation shaft portion 28A.

The second member 29 is formed of a material such as metal or resin and includes a shaft portion 29A having substantially a cylindrical shape and a rotation shaft portion 29B having substantially a cylindrical shape and being formed at an end of the shaft portion 29A. The central axis line of the shaft portion 29A is perpendicular to the central axis line of the rotation shaft portion 29B.

The second member 29 is attached to the first member 28 so that the axis line of the shaft portion 29A and the axis line of the rotation shaft portion 29B are perpendicular to the central axis line of the rotation shaft portion 28A of the first member 28. The second member 29 can rotate in a predetermined range about the axis line of the rotation shaft portion 29B with respect to the first member 28 due to a notch 28B formed in the first member 28 so as not to interfere with the shaft portion 29A.

The operation member fixing portion 30 includes a first arm 31 protruding to both sides of a first direction and a second arm (not shown) protruding to both sides of a second direction perpendicular to the first arm. Ends of four operation members 14 extending from the insertion section 10 are fixed to both ends in the longitudinal directions of the first arm 31 and the second arm. A connection member 15 is attached to an end of each operation member 14. A bearing member 32 to which the corresponding connection member 15 is attached is disposed at both ends in the longitudinal directions of the first arm 31 and the second arm. The operation members 14 are connected and fixed to the operation member fixing portion 30 by inserting the connection members 15 into the corresponding bearing members 32.

As shown in FIG. 2, the rocking member 25 is attached to the second end 26B of the rocking member receiving portion 26 so that the central axis line of the shaft portion 29A of the second member 29 is substantially coaxial with the central axis line of the guide portion 27 of the frame 24. The four operation members 14 extending from the insertion section 10 are connected to the operation member fixing portion 30 via the guide portion 27. The shape of the frame 24 is set so as not to interfere with the rocking of the rocking member 25 and the accompanying pushing and pulling (extend and retract) of the operation members 14.

The first joystick 21 is attached to the second member 29 so as to be substantially coaxial with the shaft portion 29A of the second member 29. Accordingly, by inclining the first joystick 21 in any direction, it is possible to rock the rocking member 25 relative to the frame 24 and thus to cause the operation members 14 connected to the operation member fixing portion 30 to extend and retract in the longitudinal direction of the insertion section 10. As a result, it is possible to flex the flexible portion 13 in the opposite direction of the direction in which the first joystick 21 is inclined.

The second joystick 22 is an electrical operation mechanism of which one end is attached to a board. The inclined direction is input to the board, whereby a cursor moves in the direction.

As shown in FIG. 1, the display unit 40 has a known configuration including a display 41 such as an LCD and a control board (to be described later) controlling the display of the display unit 41. The example where the display unit 40 is received in the chassis 61 will be described in detail in describing the chassis unit 60.

The chassis unit 60 includes a chassis 61 receiving the operation unit 20 and the display unit 40, a reinforcing member 62 attached to a connection portion of the chassis 61 and the insertion section 10, and a holder (self-stand assist member) 63 attached to the base end of the insertion section 10.

The chassis 61 includes an upper section 64 formed of resin or the like and mounted with the display unit 40 and a lower section 65 connected to the upper section 64 and mounted with the operation unit 20.

Figure 3:
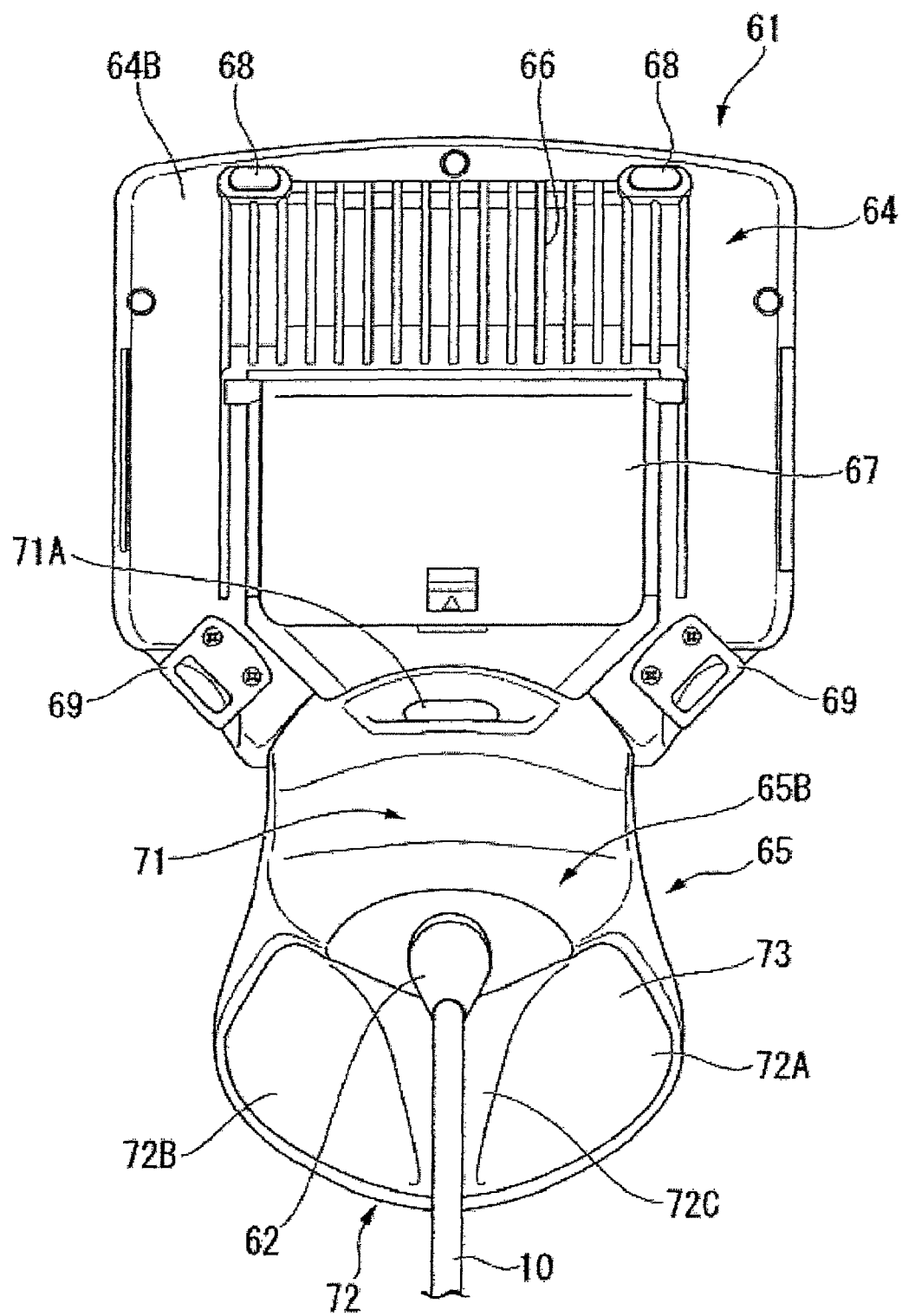
FIG. 3 is a rear view illustrating a chassis of the endoscopic device.

FIG. 3 is a rear view of the chassis 61, where the holder 63 shown in FIG. 1 is removed. As shown in FIGS. 1 and 3, the upper section 64 is formed in a substantially rectangular parallelepiped corresponding to the shape of the display 41 of the display unit 40 and the display 41 is disposed on the front surface 64A thereof. On the rear surface 64B of the upper section 64, heat-radiating fins 66 are disposed on the upper side and a lid 67 of a battery receiver (to be described later) is disposed on the lower side. Two ground-contact members 68 formed of rubber or elastomer are attached to the upper edge of the rear surface 64B, whereby the friction coefficient is high. Clasps 69 used to attach accessories such as straps are attached to the lower edge connected to the lower section 65.

Figure 4:
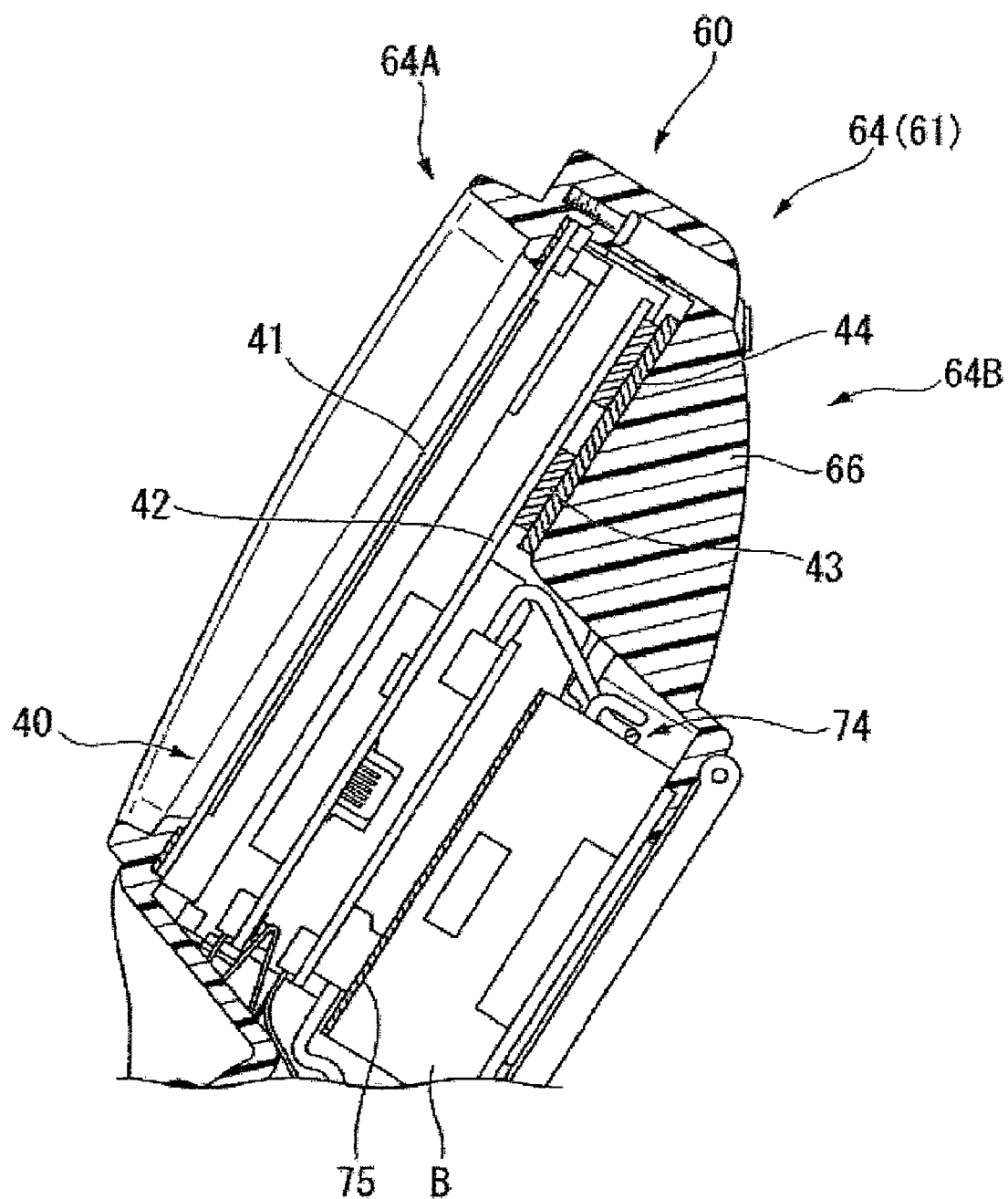
FIG. 4 is a sectional view taken along a front-and-rear direction of an upper section of the chassis.
Figure 5:
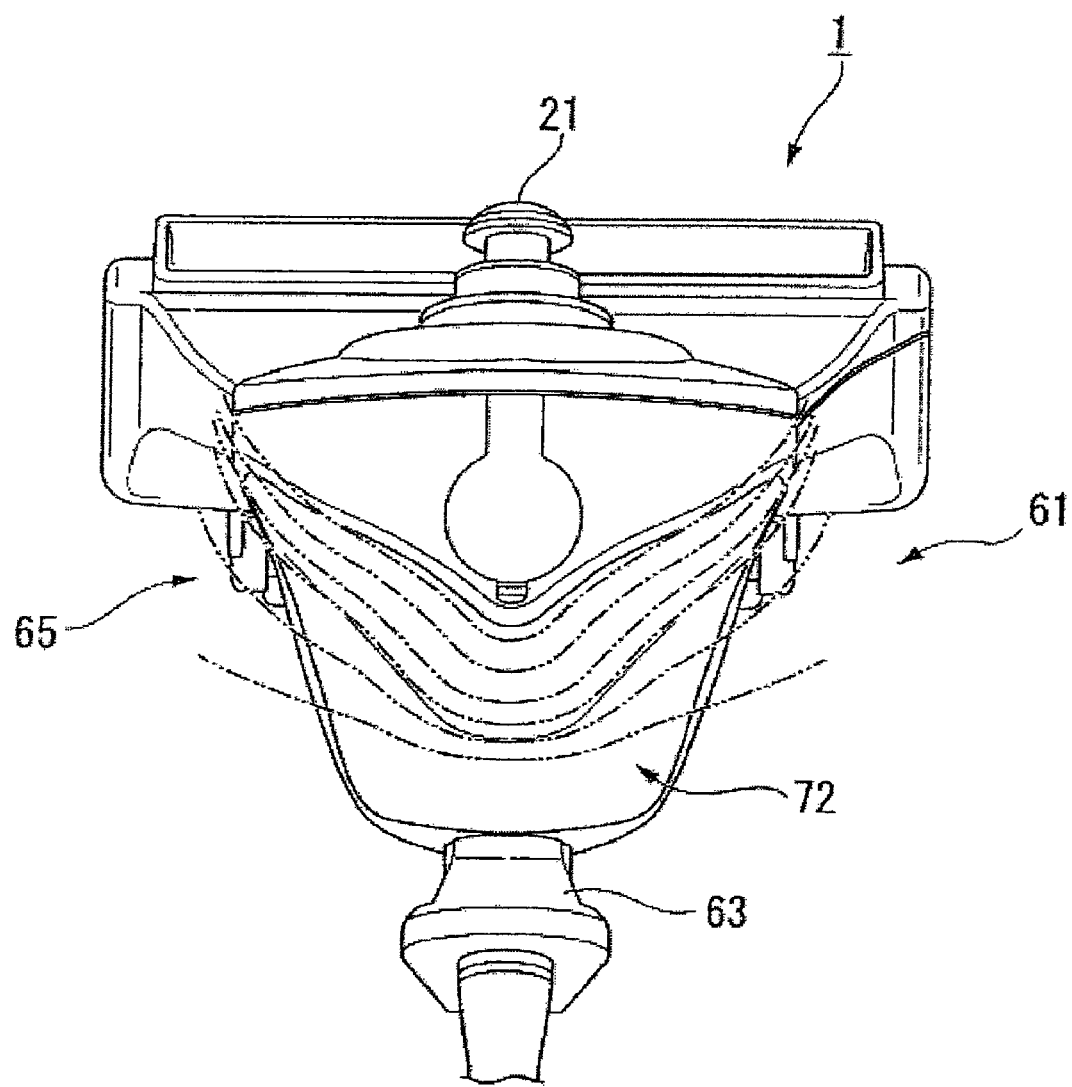
FIG. 5 is a bottom view of the chassis.

FIG. 4 is a sectional view of the upper section 64 taken along the front-end-rear direction. In the upper section 64, the display unit 40 is received in the front surface 64A and a battery B is disposed in the rear surface 64B. A control board 42 including an IC 43 is connected to the display 41 and is received in the rear surface of the display 41 with the IC 43 facing the rear surface 64B.

The IC 43 generating heat at the time of operation is received at a position close to the fins 66 disposed at the upper part of the rear surface 64B, and a thermal-conduction sheet 44 is interposed between the IC 43 and the fin 66.

The battery B is received in the battery receiver 74 formed in the back of the control board 43. The battery receiver 74 has an opening in the rear surface 64B of the upper section 64 that is closed by the lid 67. By positioning the opening in the rear surface 64B, the battery B can be easily inserted and removed from the chassis 61.

Figure 15A:
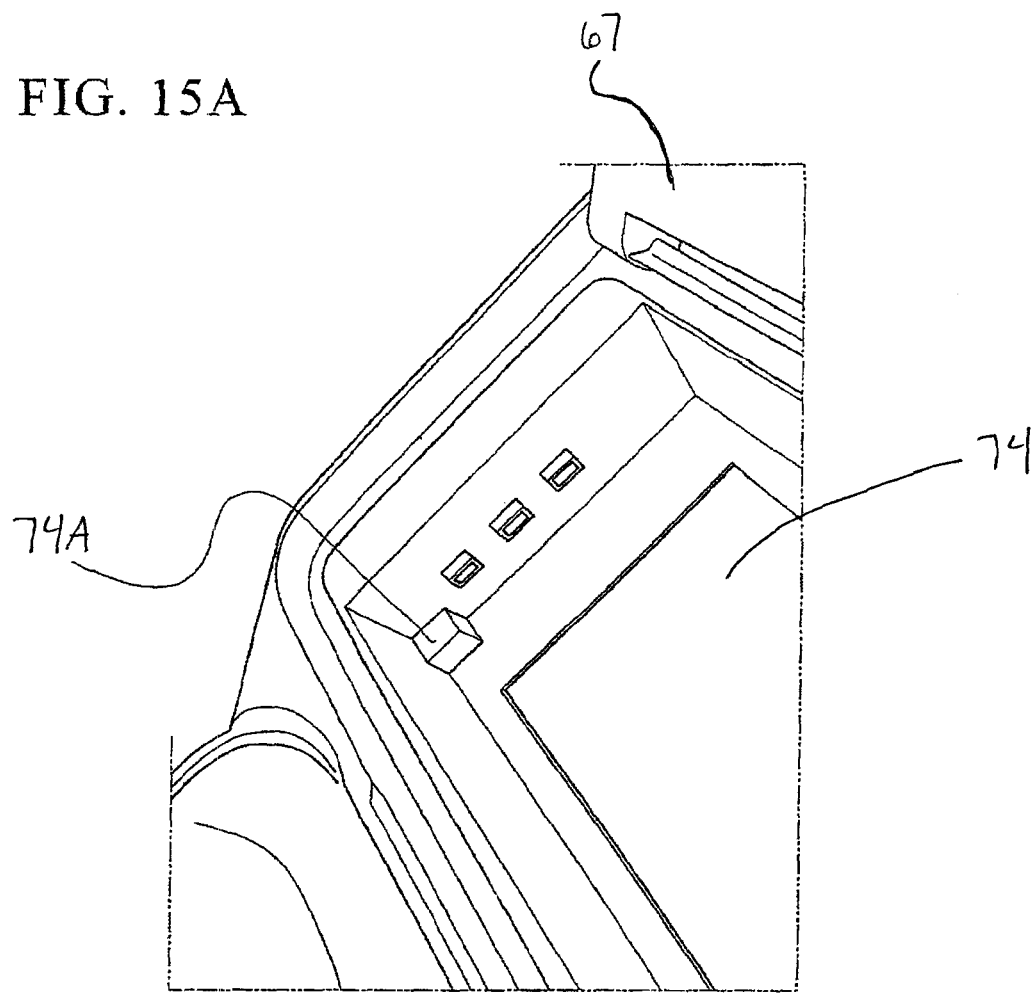
FIG. 15A illustrates the interior of a battery receiver according to an embodiment of the invention.
Figure 15B:
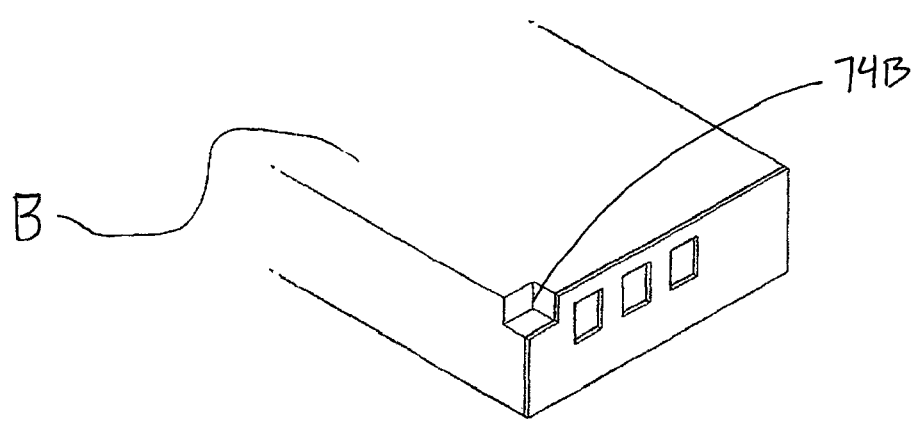
FIG. 15B illustrates a battery according to an embodiment of the invention.

The battery receiver 74 and the battery B have structures such that the battery B can be fitted into the battery receiver 74 in only one way. That is, only one orientation of the battery B with respect to the battery receiver 74 allows the battery B to fit in the battery receiver 74. For example, as shown in FIGS. 15A and 15B, the battery receiver 74 has a convex portion 74A that fits into a concave portion 74B in the battery B. As a result, if the user inserts the battery B incorrectly, the convex portion 74A of the battery receiver 74 will not fit into the battery B, and the battery B will therefore not fit in the battery receiver 74. The convex portion 74A may serve as a stopper that sets the battery B in a predetermined position within the battery receiver 74. Alternatively, for example, the battery B may have the convex portion, and the battery receiver 74 may have the concave portion.

A thermal-insulation sheet 75 is disposed on the wall surface of the battery receiver 74 close to the front surface, whereby the heat generated from the battery B is hardly transmitted to the display unit 40. According to this configuration, the IC 43 and the battery B generating heat at the time of using the endoscopic device 1 are separated from each other. The heat generated from the IC 43 is efficiently radiated to the outside from the fin 66s via the thermal-conduction sheet 44, and the heat generated from the battery B is hardly transmitted to the display unit 40 as described above. As a result, it is possible to embody a structure in which two heating members of the IC 43 and the battery B are received in the upper section 64 but do not adversely influence the display or the like of the display 41.

In addition to being positioned at the upper side of the rear surface 64B, the heat radiating fins 66 can be positioned to at least partially surround in the battery B (or, more specifically to at least partially surround the battery receiver 74). For example, heat radiating 66 are also disposed on left and right sides of the battery receiver 74 in FIG. 3, so that the heat radiating fins 66 surround the battery B (battery receiver 74) on three sides.

The battery receiver 74 is positioned such that battery B is housed adjacent to a position where the upper section 64 and the lower section 65 are connected. In addition, the battery receiver 74 is located so that a distance between the battery B and the first joystick 21 is less than a distance between the display 41 and the first joystick 21. Moreover, the battery receiver 74 is positioned such that a distance between the display 41 and the battery B is less than a distance between the display 41 and a line connecting an upper edge of the upper section 64 and a connection portion where the insertion section 10 is connected to the lower section 65.

The lower section 65 is a part which is held by a user's hand at the time of using and operating the endoscopic device 1. As shown in FIG. 1, the lower section 65 is connected to the upper section 64 so that the front surface 64A of the upper section and the front surface 65A of the lower section 65 form a predetermined angle so that the user can see the display 41 well at the time of holding the lower section 65.

The peripheral edge of the front surface 65A has a curved shape which is narrowed at a middle part in the vertical direction and is slowly widened toward the lower edge. The peripheral edge is laterally symmetric so as to appropriately hold the lower section 65 with any of the right and left hands.

Out of two joysticks of the operation unit 20, the second joystick 22 is disposed on the lower side of the front surface 65A and the first joystick 21 is disposed on the upper side of the second joystick 22. The line connecting the first joystick 21 and the second joystick 22 passes through the center in the lateral direction (the direction perpendicular to the vertical direction of the chassis 61) of the display unit 40 in the front view of the chassis 61. The distal end of the first joystick 21 protrudes from the front surface 65A by a predetermined length so as to be easily operated by the user holding the lower section 65. The second joystick 22 protrudes from the bottom of a concave portion 70 disposed in the front surface 65A and the height thereof is set so as for the distal end not to protrude from the front surface 65A.

As shown in FIG. 3, the insertion section 10 is connected to the rear surface 65B of the lower section 65. The insertion section 10 extends from the middle part in the vertical direction of the rear surface 65B. A first slope (the first face) 71 rising toward the insertion section 10 is formed in the rear surface 65B above the insertion section 10 and a second slope (the second face) 72 rising toward the insertion section 10 is formed below the insertion section 10. The rear surface 65B of the lower section 65 has a convex shape toward the rear side in the side view of the chassis 61 due to the first slope 71 and the second slope 72. In this configuration, the rear surface 65B out of the rear surface of the chassis 61 serves as a part (grip face) on which fingers are rested when the user holds the chassis 1.

The first slope 71 is set to such a size that an index finger and a middle finger of a hand with a standard size are vertically arranged and simultaneously rested thereon, and serves as a first finger rest. A freeze/record button 71A used to record an image acquired by an imaging capturing device of the insertion section 10 as a still image or a moving image is disposed in the first slope 71 and can be operated with an index finger when the user holds the lower section 65.

The second slope 72 is set to such a size that a ring finger and a little finger of a hand with a standard size are vertically arranged and simultaneously rested thereon, and serves as a second finger rest. Since the second slope 72 is formed in the lower section 65, as indicated by a two-dot chained line in FIG. 5, the sectional area parallel to the lateral direction of the chassis 61 and perpendicular to the vertical direction thereof slowly becomes smaller toward the lower end. The second slope 72 includes a first holding face 72A and a second holding face 72B sloped toward the peripheral edges in the lateral direction of the rear surface 65B and a third holding face 72C extending to the lower peripheral edge of the rear surface 65B and connecting the first holding face 72A and the second holding face 72B to each other. Accordingly, the second slope 72 has a shape convex toward the rear surface 65B in the bottom view of the chassis 61. Frictional members 73 formed of elastically-deformable material such as rubber or elastomer are attached to the faces of the second slope 72. Accordingly, the friction coefficients of the holding faces are higher than the other faces of the chassis 61.

Figure 6:
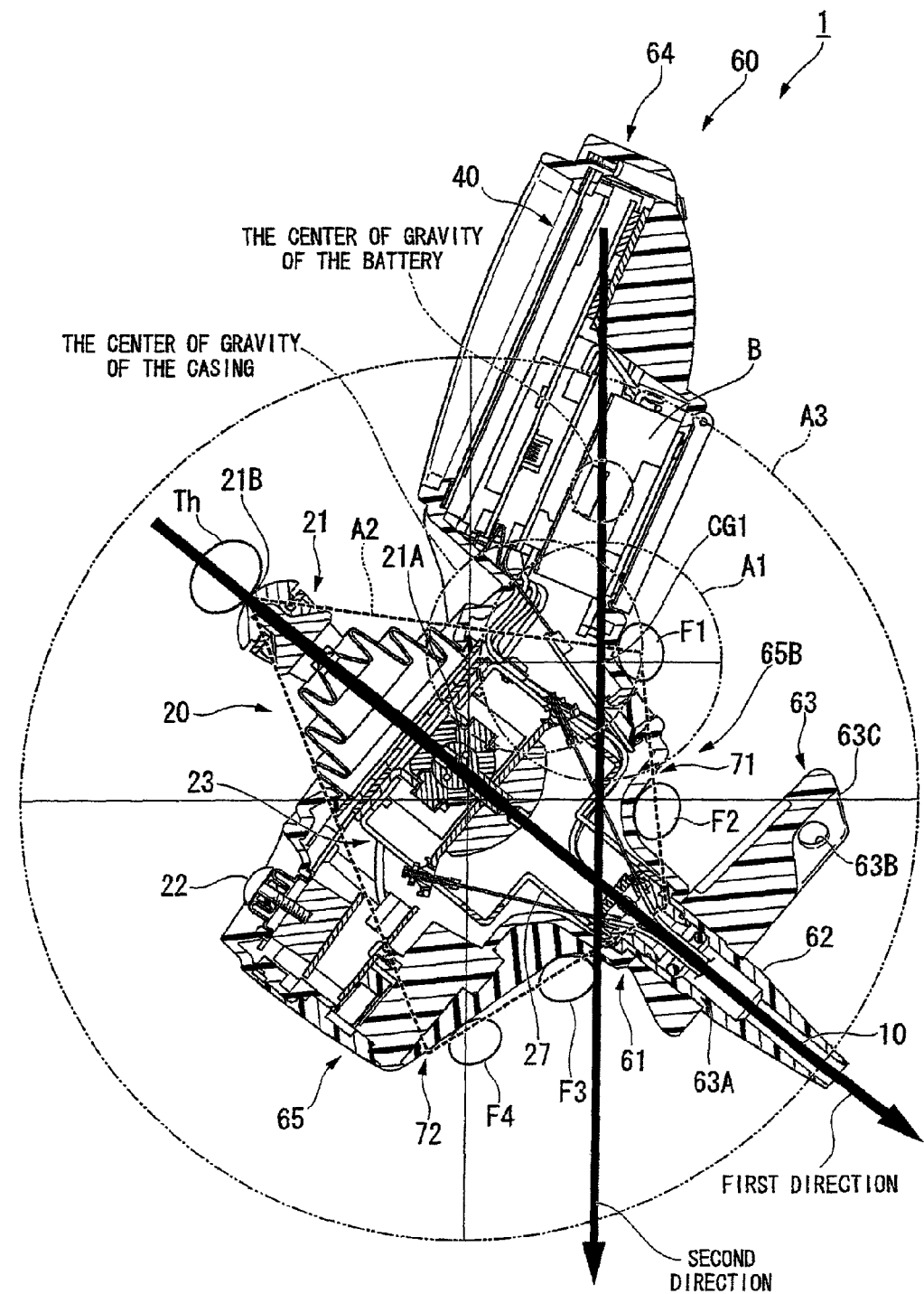
FIG. 6 is a sectional view of an operation unit, a display unit, and a chassis unit of the endoscopic device taken along the central axis line of an insertion section.

As shown in FIG. 6, the size of the second slope 72 in the vertical direction of the chassis 61 is greater than that of the first slope 71.

The reinforcing member 62 is formed in a substantially cylindrical shape of which one end is reduced in outer diameter in a tapered shape, and is disposed to cover the base end of the insertion section 10 connected to the chassis 61 and the periphery thereof. The reinforcing member 62 has constant rigidity and thus the part of the insertion section 10 covered with the reinforcing member 62 is maintained in a straight line shape. That is, the reinforcing member 62 serves as a bending stopper preventing the covered insertion section 10 from being bent at a large angle.

FIG. 6 is a sectional view of the operation unit 20, the display unit 40, and the chassis unit 60 taken along the central axis line of the insertion section 10. The holder 63 is formed of resin or the like and includes a first through-hole 63A with a large diameter formed at a first end and a second through-hole 63B with a small diameter formed at a second end as shown in FIG. 6. The holder 63 is attached to a connection portion between the insertion section 10 and the chassis 61 with the reinforcing member 62 inserted into the first through-hole 63A. The inner diameter of the second through-hole 63B is slightly larger than the outer diameter of the insertion section 10 and thus can maintain the insertion section 10 inserted therethrough. A ground-contact face 63C is disposed at the second end of the holder 63 and details thereof will be described later.

As shown in FIG. 6, the flexing mechanism 23 is received in the lower section 65 of the chassis 61 so that the guide portion 27 is located on the rear surface 65B, and the central axis line of the insertion section 10 and the first joystick 21 in a neutral state of non-operation are coaxial or substantially coaxial with each other.

When the battery B is received in the upper section 64 of the chassis 61, the center of gravity of the endoscopic device 1 other than the insertion section 10 is a designed center of gravity position CG1 shown in FIG. 6. The actual position of the center of gravity may be slightly shifted due to allowable manufacturing errors of individual products, but should preferably be situated in an area A1, which is located within a predetermined radius from the designed center of gravity position CG1 and includes the portion where the upper section 64 and the lower section 65 are connected.

Moreover, when the battery B is received in the upper section 64, a line connecting (or extending through) a center of gravity of the battery B (see FIG. 6) and the center of gravity of the endoscopic device 1 other than the insertion section 10 extends in a direction (refer to the "Second Direction" in FIG. 6) that intersects a direction in which the insertion section 10 extends from the lower section 65 (refer to the "First Direction" in FIG. 6).

When the battery B is removed from the upper section 64 of the chassis 61, the location of the center of gravity of the endoscopic device 1 (other than the insertion section 10) shifts downward and to the left in the view shown in FIG. 6. That is, when the battery B is removed from the upper section 64 of the chassis 61, the location of the center of gravity of the endoscopic device 1 (other than the insertion section 10) shifts toward the inside of the lower section 65.

Figure 7:
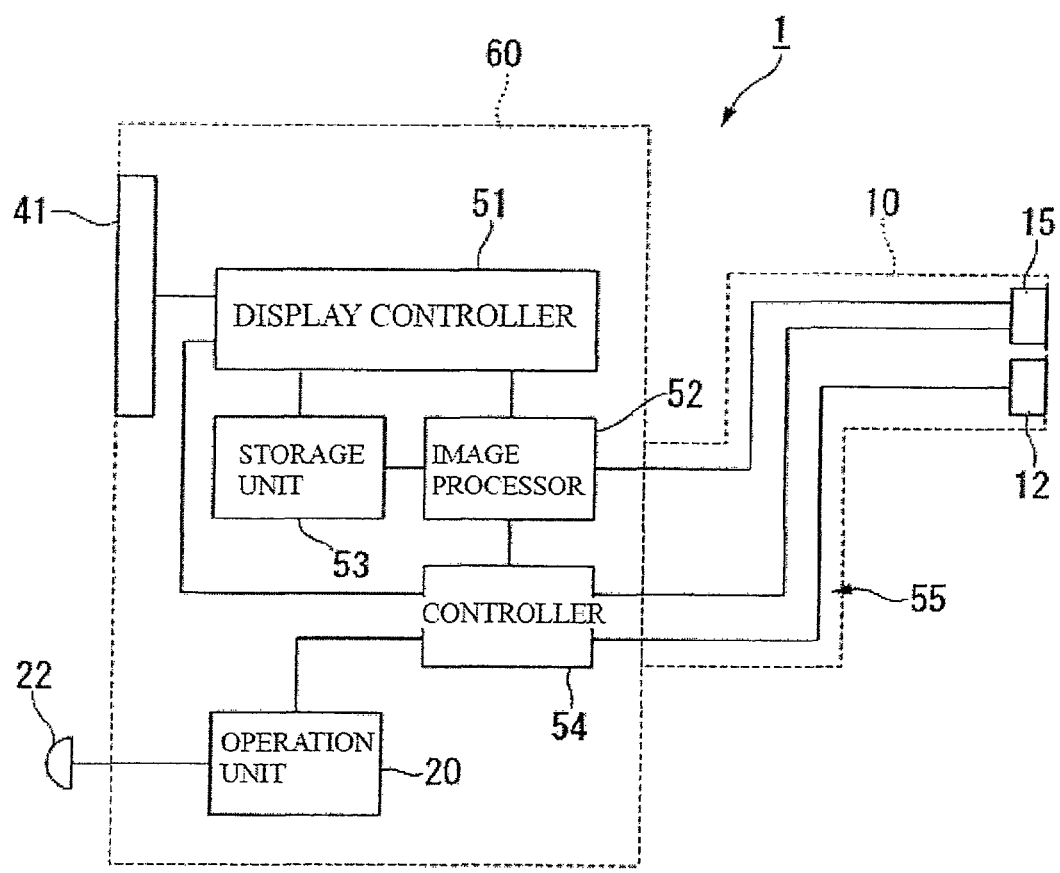
FIG. 7 is a functional block diagram illustrating the endoscopic device.

FIG. 7 is a functional block diagram illustrating the endoscopic device 1. The endoscopic device 1 includes an image processor 52 processing an image signal acquired by the image capturing mechanism 15 of the insertion section 10, a storage unit 53 storing the acquired still image or moving image, and a controller 54 controlling the entire operation of the endoscopic device 1 including the light intensity adjustment of the illumination mechanism 12, in addition to a display controller 51.

The image processor 52 and the controller 54 are stored, for example, in an IC (not shown) attached to the control board 42. Various known storage mediums can be used as the storage unit 53, which may be detachably attached to the chassis unit 60. The image capturing mechanism 15 and the illumination mechanism 12 are connected to the image processor 52 or the controller 54 via a line 55 extending to the inside of the chassis unit 60 through the insertion section 10. The second joystick 22 of the operation unit 20 is electrically connected to the controller 54 via a substrate or the like not shown.

The operation of the endoscopic device 1 having the above-mentioned configuration will be described below.

A user starts up the endoscopic device 1 in the state where the battery B is received in the battery receiver 74 and inserts a distal end of the insertion section 10 into a sample or an access channel to the sample up to an observation target site.

When it is intended to change the direction of the distal end of the insertion section 10, the insertion section 10 is flexed in a desired direction by operating the first joystick 21 of the operation unit 20 to cause the operation member 14 connected to the flexing mechanism 23 to extend or retract.

At this time, the user surrounds and holds the lower section 65 of the chassis 61 with his or her dominant hand and operates the end of the first joystick 21 protruding from the front surface 65A with his or her thumb. An example of the positional relation of the user's fingers and the chassis unit 60 at the time of operation is shown in FIG. 6. At the time of operation, at least an index finger F1 is located on the first slope 71 of the rear surface 65B of the lower section and a little finger F4 is located on the second slope 72 in the side view of the chassis 61. Accordingly, the connection portion of the insertion section 10 and the chassis unit 60 is located between the index finger F1 and the little finger F4 and the insertion section 10 extends from the rear surface 65B which is a grip face.

In the example shown in FIG. 6, a middle finger F2 in addition to the index finger F1 is located on the first slope 71 and a ring finger F3 in addition to the little finger F4 is located on the second slope 72.

When the distal end of the insertion section 10 reaches the observation target site, the user observes or inspects the sample while operating the operation unit 20. As needed, the user operates the freeze/record button 71A to record a still image or a moving image of the target site. The acquired various images are stored in the storage unit 53.

Figure 8:
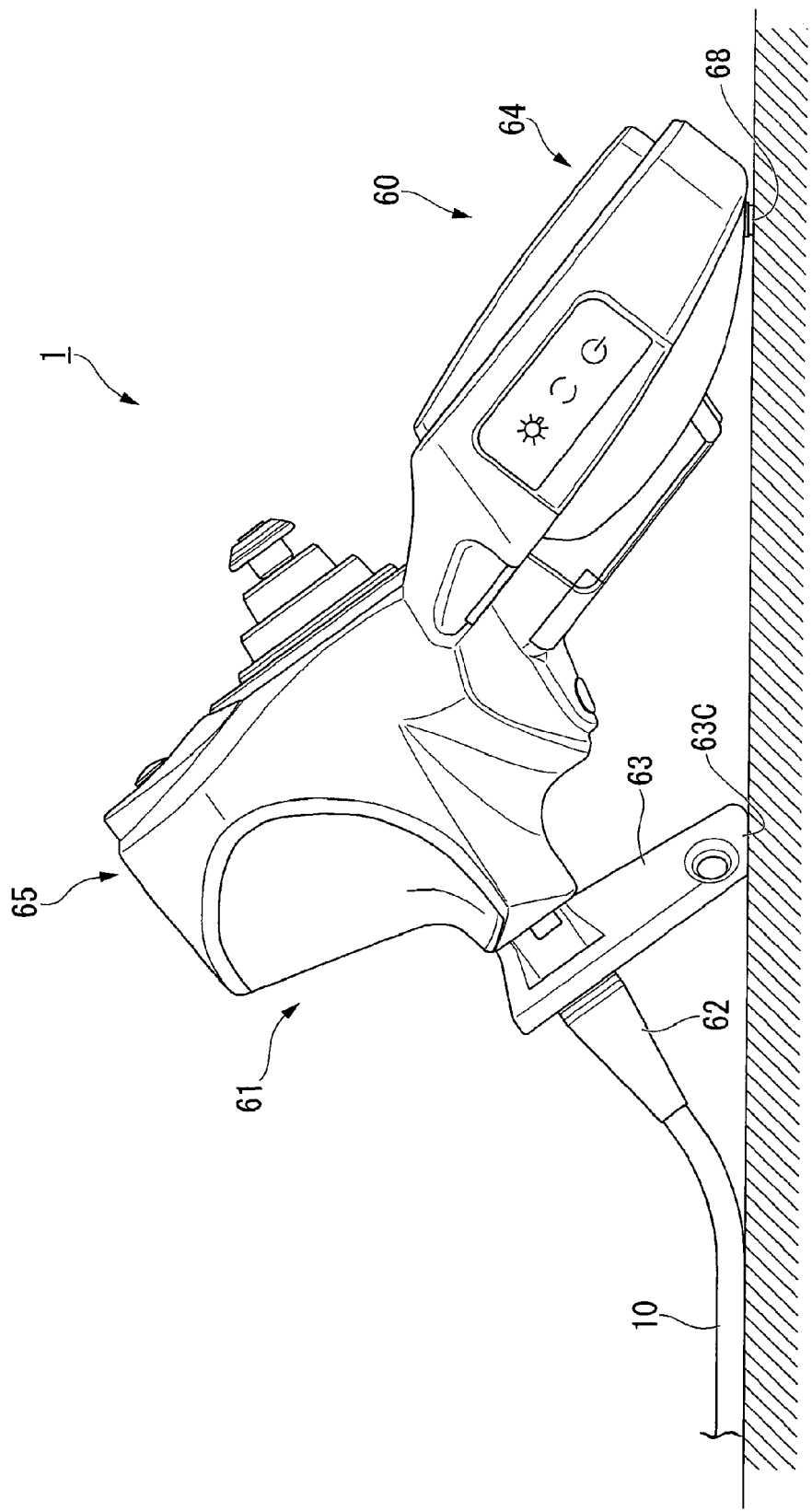
FIG. 8 is a diagram illustrating a state where the endoscopic device comes in contact with the ground in an inversion mode.

When the hand holding the chassis 61 is tired due to the increase in use time or the like, the chassis 61 can be placed on a ground, a desk, or the like for operation. When the chassis 61 is placed, as shown in FIG. 8, two ground-contact members 68 disposed in the upper section 64 and the connection portion of the insertion section 10 and the chassis 61, that is, the boundary between the reinforcing member 62 and the insertion section 10 and a predetermined range around the boundary, are brought into contact with the ground. Accordingly, the chassis 61 appropriately self-stands with the upper section 64 located on the lower side and the lower section 65 located on the upper side.

Since the base end of the insertion section 10 extending from the chassis 61 is maintained in a straight line shape by the reinforcing member 62, the chassis appropriately self-stands without the holder 63. However, as shown in FIG. 8, when the second end of the holder 63 is placed to face the upper section 64 of the chassis 61, the ground-contact face 63C is located on the ground-contact face of the chassis 61 defined by the ground-contacting connection portion and the ground-contact member 68. As a result, the holder 63 can appropriately support the self-standing of the chassis 61 and can maintain the chassis 61 more stably. Hereinafter, the state where the endoscopic device 1 is used with the chassis 61 placed in this way is referred to as an "inversion mode".

At the time of placing the chassis 61 in the above-mentioned way, the user inputs a predetermined operation by the use of the operation unit 20 and switches the display mode of the screen. The display controller 51 switches the display of the display 41 from a standard mode shown in FIG. 9A to the display mode corresponding to the inversion mode shown in FIG. 9B in response to the input.

Figure 9A:
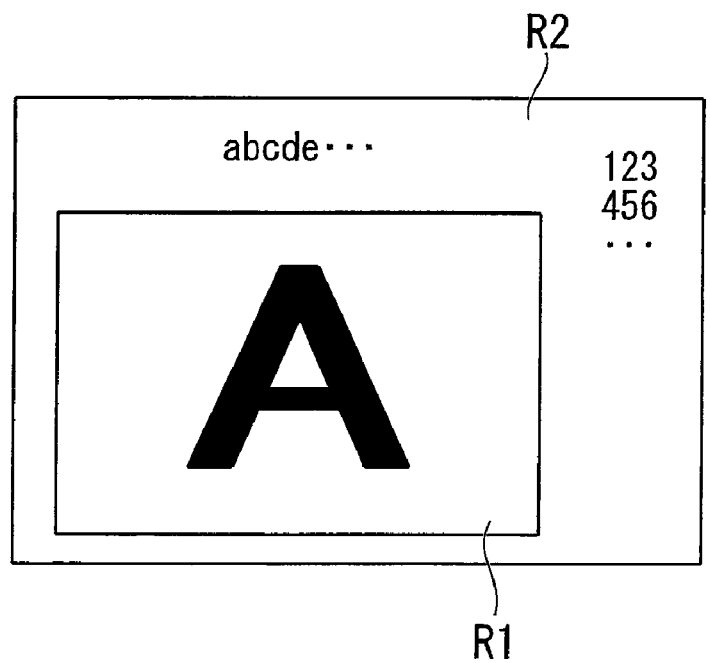
FIG. 9A is a diagram illustrating an example of a screen display in a standard mode of the endoscopic device.
Figure 9B:
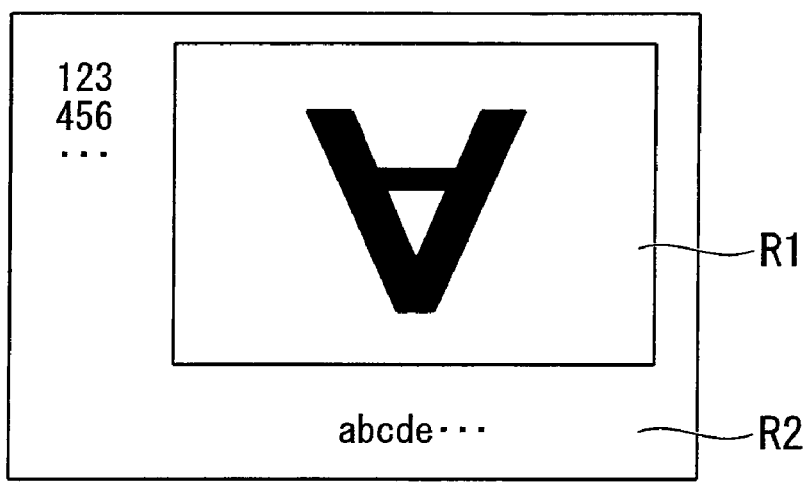
FIG. 9B is a diagram illustrating an example of the screen display in the inversion mode of the endoscopic device.

As shown in FIG. 9A, in the standard mode, the image acquired by the image capturing mechanism 15 is displayed in a first region R1 and text information such as an operation menu or various parameters is displayed in a second region R2. In the inversion mode shown in FIG. 9B, the user views an upset display. Accordingly, the text information displayed in the second region R2 is vertically inversed from the standard mode state. On the other hand, the image displayed in the first region R1 is not vertically inversed in the inversion mode. This is to maintain the correspondence between the image and the operation of the first joystick 21. This is also to store the vertically-unified image in the storage unit 53 even when the image is recorded in any one of the standard mode and the inversion mode at the time of operating the freeze/record button 71A to record an image.

Figure 10A:
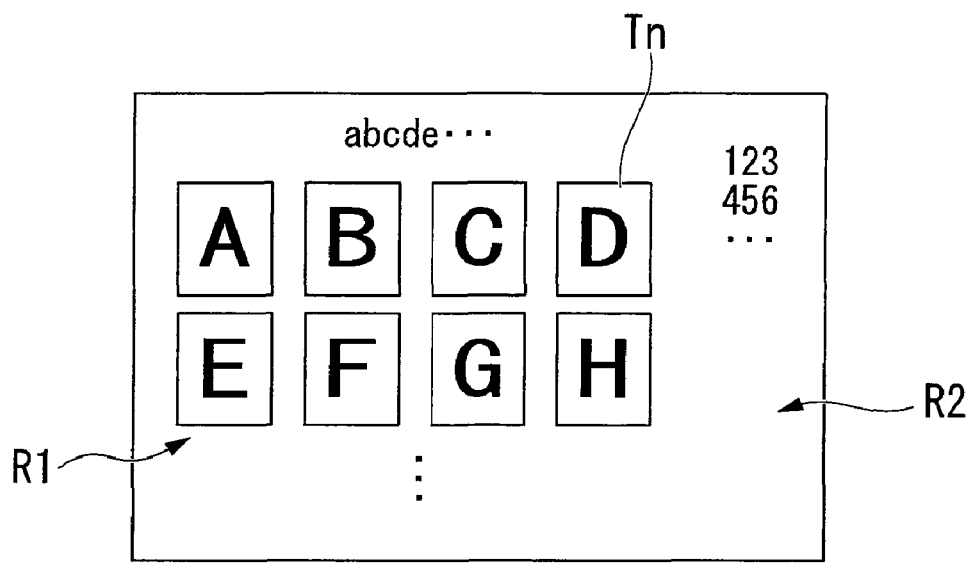
FIG. 10A is a diagram illustrating an example of the screen display in the standard mode.
Figure 10B:
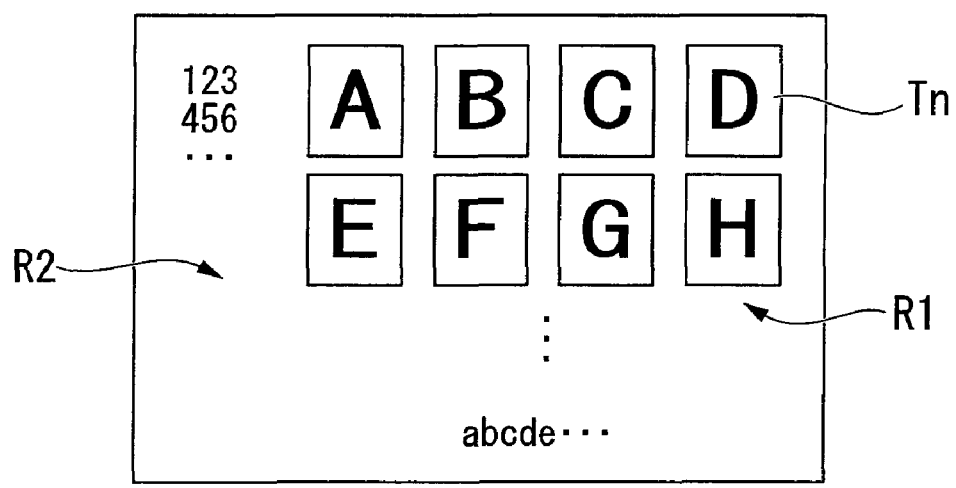
FIG. 10B is a diagram illustrating an example of the screen display in the inversion mode.

On the other hand, since the above-mentioned consideration is not necessary for a thumbnail picture representing a list of images stored in the storage unit 53, the images are vertically inverted and displayed in the first region R1 in the inversion mode shown in FIG. 10B. As a result, the direction of thumbnail images Tn which are viewed by the user is the same as the standard mode shown in FIG. 10A. In the case of a retrieval picture (not shown) displaying an image corresponding to a thumbnail image Tn selected from the thumbnail picture, the image is vertically inverted and displayed in the inversion mode.

As described above, in the endoscopic device 1 according to this embodiment, since the first joystick 21 in the neutral state and the insertion section 10 connected to the chassis unit 60 are coaxially arranged, the extend and retract amounts of the operation members 14 become uniform to appropriately flex the flexible portion 13 at the time of performing a flexing operation by the use of the mechanical flexing mechanism 23 employing the operation members 14.

In the rear surface 65B, to which the insertion section 10 is connected, of the lower section 65 of the chassis 61 in which the flexing mechanism 23 is received, the first slope 71 and the second slope 72 are formed above and below of the insertion section 10, respectively. Accordingly, the rear surface 65B has a convex shape rising toward the insertion section 10 in the side view of the chassis 61. Therefore, the user's hand holding the lower section 65 grasps the rear surface 65B with the palm of the hand maintained in a concave shape, at least one finger out of four fingers other than the thumb is placed on each of the first slope 71 and the second slope 72 with the insertion section 10 interposed therebetween in the vertical direction.

As a result, the force amount such as a moment acting on the chassis unit 60 due to the long insertion section 10 can be appropriately received by the user's hand regardless of the acting direction, thereby stably holding the chassis 61.

Since the center of gravity of the endoscopic device 1 other than the insertion section 10 is set within the region A1, the user can appropriately hold the chassis unit 60 with the hand holding the lower section 65 and can stabilize the positions of the upper front surface 64A and the lower front surface 65A. That is, states where it is difficult to view the display unit 40 and to operate the operation unit 20 do not easily occur, such as a state where the upper front surface 64A is inclined toward the rear side or a state where the lower front surface 65A is parallel to the vertical direction. As a result, it is possible to hold the chassis unit 60 in the state where the display 41 can be viewed well and the operation unit 20 can be easily operated.

Due to the above-mentioned shape of the lower rear surface 65B, the rocking center 21A of the first joystick 21 is located within the region A2 defined by the first slope 71, the second slope 72 and the distal end 21B of the first joystick 21 protruding to the front surface 65A on which the user's fingers are rested at the time of holding the chassis 61 in the side view of the chassis 61 shown in FIG. 6. Accordingly, it is possible to provide an endoscopic device which can appropriately prevent the chassis unit 60 from being shaken due to the force amount acting on the chassis unit 60 at the time of operating the first joystick 21 and can reduce the fatigue even with a long-term operation.

Since the second slope 72 includes the first holding face 72A and the second holding face 72B, the distal ends of the fingers (for example, the ring finger F3 and the little finger F4) placed on the second slope 72 are arranged along one of the first holding face 72A and the second holding face 72B at the time of holding the lower section 65.

Figure 11:
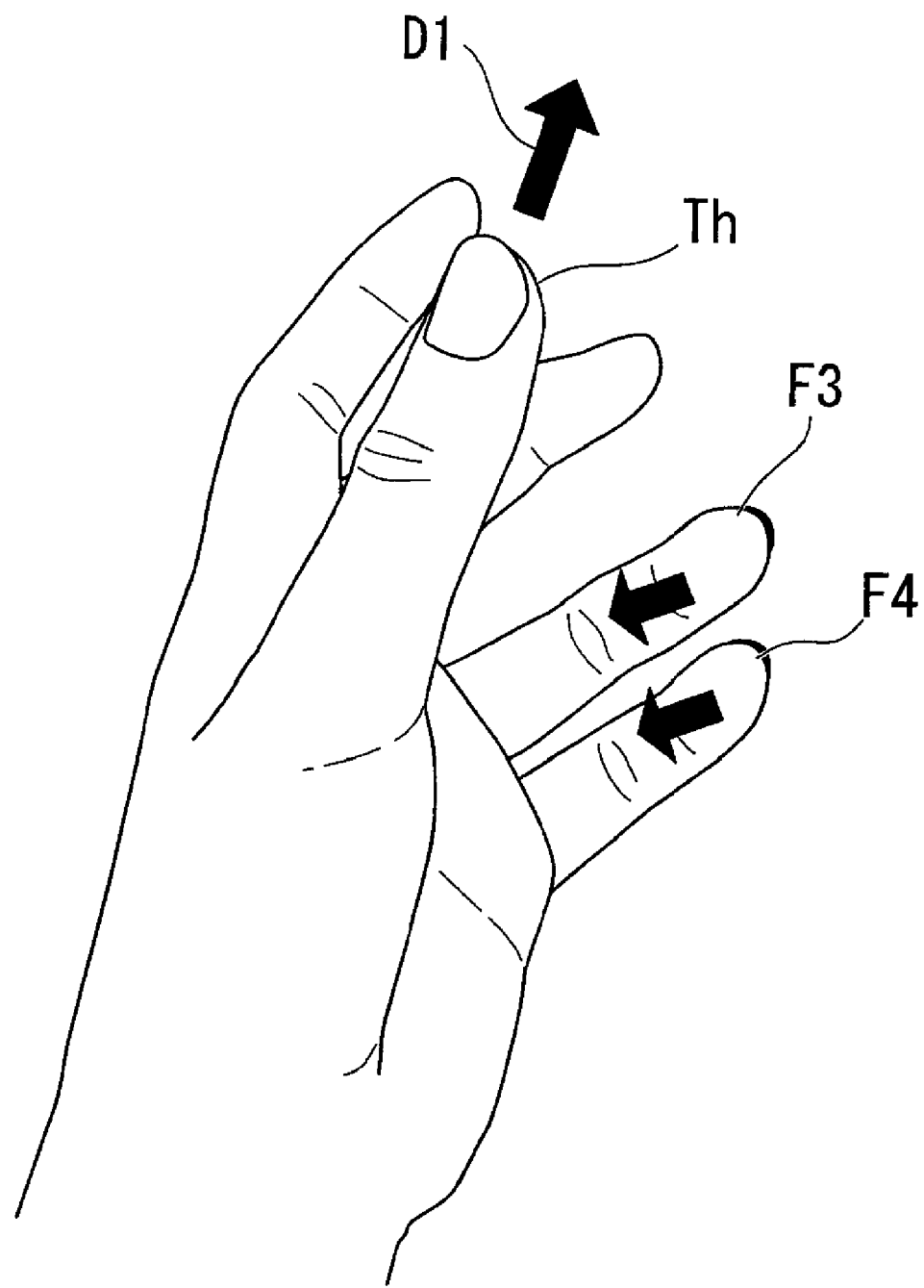
FIG. 11 is a diagram illustrating an example of a user's hand holding the chassis of the endoscopic device.

Accordingly, as shown in FIG. 11, the fingers F3 and F4 placed on the second slope 72 are substantially opposed to the thumb Th. As a result, at the time of inclining the first joystick 21 with the thumb Th in the direction (for example, in the direction of arrow D1 in FIG. 11) going away from the hand, such as a direction in which the thumb Th extends, the force amount, which acts with the inclination operation, for inclining the chassis 61 can be appropriately received by the ring finger F3, the little finger F4, and the like and the operation can be carried out while maintaining the stabilized state of the chassis 61. Here, since the size of the second slope 72 in the vertical direction of the chassis 61 is greater than that of the first slope 71, the fingers placed on the second slope 72 can be arranged with an appropriate gap therebetween, thereby more stably holding the chassis in use.

The above-mentioned effect can be exhibited even when the flexing mechanism is electrically driven by a motor or the like. However, since the mechanical flexing mechanism employing only the operation members generates a greater force amount with the operation of the first joystick 21, the effect is more greatly exhibited in the endoscopic device according to this embodiment.

This effect is similarly exhibited even when a button or the like is disposed in the extending direction of the thumb Th in the operation unit 20 and the button is operated. FIG. 11 shows an example where the holding and the operation are performed with a left hand. In this case, the distal ends of the fingers placed on the second slope 72 are located on the second holding face 72B. When the user performs the holding and the operation with the right hand, the distal ends of the fingers are located on the first holding face 72A. However, since the first holding face 72A and the second holding face 72B are arranged symmetric about the lateral center of the chassis 61, the same effect is obtained.

The friction members 73 having elasticity are attached to the first holding face 72A and the second holding face 72B. Accordingly, even when a relatively large force amount acts on the fingers placed on the second slope 72, the positional relation between the second slope 72 and the fingers is appropriately maintained. As a result, it is possible to appropriately hold the chassis unit 60 during the operation and thus to perform a stable operation.

Since the second joystick 22 protrudes from the bottom of the concave portion 70 formed in the lower face 65A and the height thereof is set so as for the distal end not to protrude from the front surface 65A, the second joystick 22 is arranged at a position, which can be easily operated with the thumb Th, around the first joystick 21 and does not interfere with the operation of the first joystick 21, thereby further improving the operability of the endoscopic device 1.

Since the chassis 61 can be appropriately made to self-stand with the upper section 64 located on the lower side and the lower section 65 located on the upper side so as to be used in the inversion mode by bringing two ground-contact members 68 disposed in the upper section 65 and the connection portion of the insertion section 10 and the chassis unit into contact with the ground, it is possible to suitably use the endoscopic device 1 for a long-term operation. Even in the inversion mode under the control of the display controller 41, it is possible to easily view the display of the display 41 and thus to appropriately use the endoscopic device.

Although the invention has been described with reference to an embodiment, the technical scope of the invention is not limited to the embodiment, but the elements may be modified in various forms or may be deleted without departing from the concept of the invention.

Figure 12:
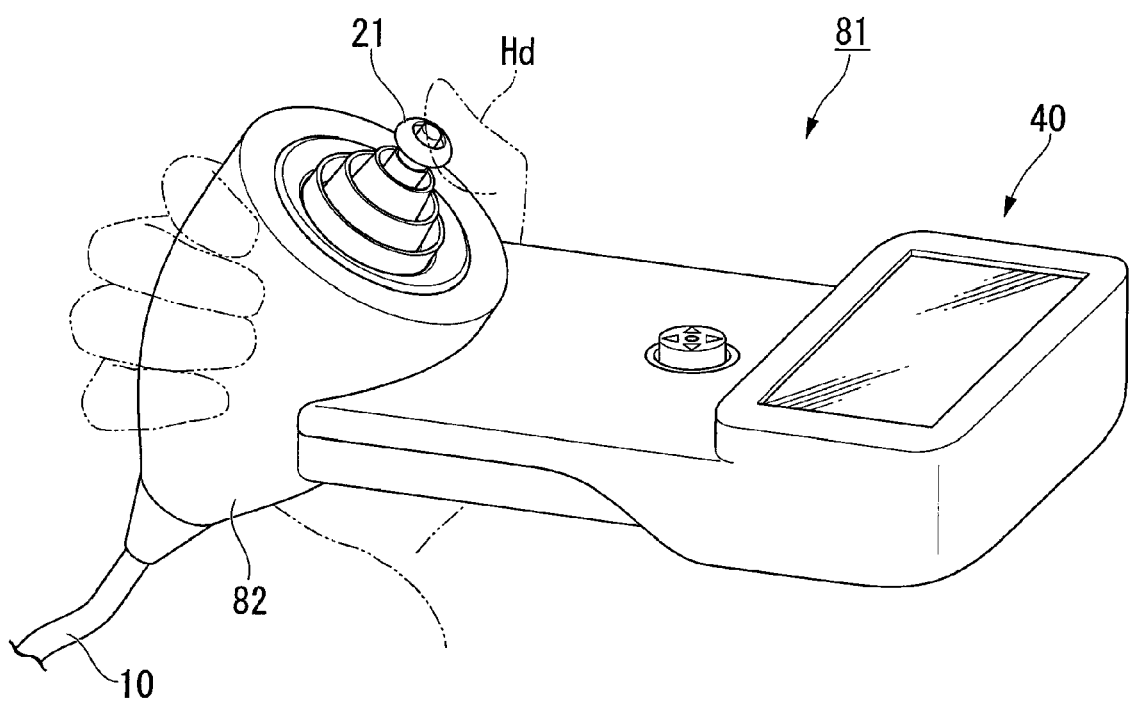
FIG. 12 is a perspective view illustrating the entire appearance of an endoscopic device according to a modification of the invention.

The grip face in the invention is not limited to the shape having the first slope and the second slope, but may have any convex shape protruding to the rear surface. In an endoscopic device 81 according to a modification shown in FIG. 12, a grip face 82 has a spindle shape convex to the rear surface. Since portions of the grip face 82 corresponding to the first face and the second face are curved but follow the curvature of the user's fingers holding the grip face 82, it is possible to appropriately arrange the fingers and to stably hold the grip face 82. In FIG. 12, the hand Hd holding the grip face 82 in a state where the first joystick 21 is located on the fingertip side and the display unit 40 is located on the hand base side is indicated by a two-dot chained line, but the display unit 40 may be located on the upper side, similarly to the above-mentioned endoscopic device 1.

Figure 13:
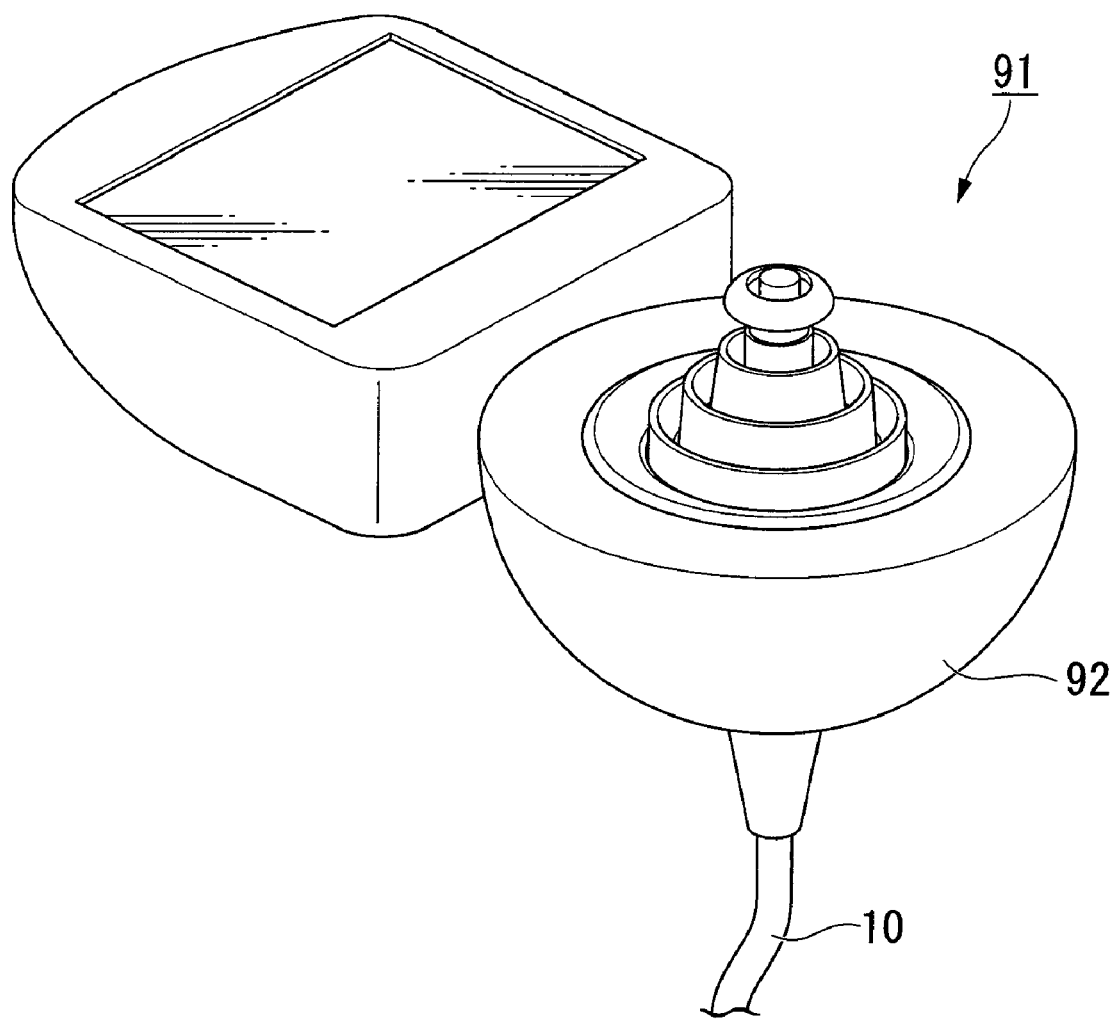
FIG. 13 is a perspective view illustrating the entire appearance of an endoscopic device according to another modification of the invention.
Figure 14A:
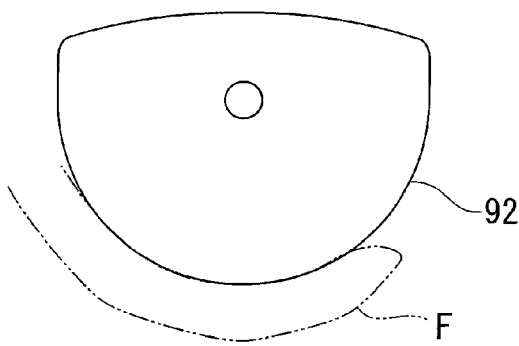
FIG. 14A is a diagram schematically illustrating the shape of a grip face in the endoscopic device according to the modification of the invention.

FIG. 13 shows an endoscopic device 91 according to another modification of the invention in which a grip face 92 has a spherical shape. Since the grip face 92 also follows the curvature of the user's fingers F holding the grip face 92 as schematically shown in FIG. 14A, it is possible to appropriately arrange the fingers F.

FIGS. 14B to 14E are bottom views (the view shown in FIG. 5) of a chassis schematically illustrating examples of the shape of a grip face.

Figure 14B:
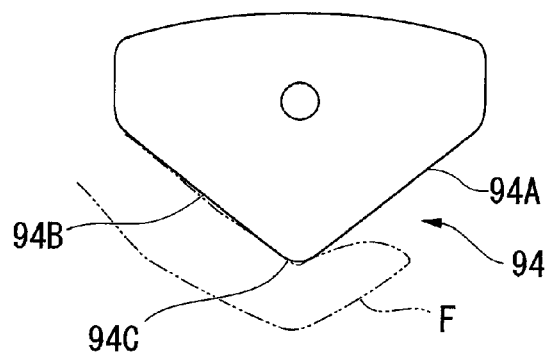
FIG. 14B is a diagram schematically illustrating the shape of a grip face in an endoscopic device according to another modification of the invention.
Figure 14C:
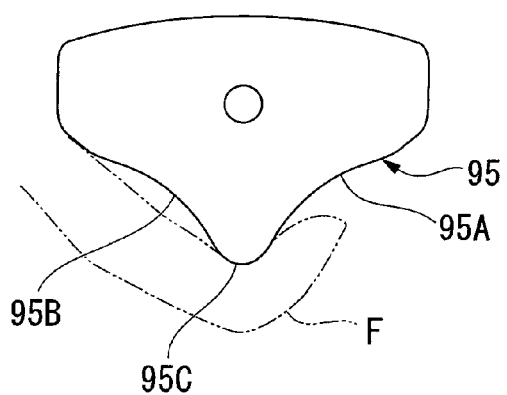
FIG. 14C is a diagram schematically illustrating the shape of a grip face in an endoscopic device according to another modification of the invention.

A grip face 94 shown in FIG. 14B and a grip face 95 shown in FIG. 14C have first holding faces 94A and 95A and second holding faces 94B and 95B rising from both lateral edges of a chassis and are convex to the rear surface in the bottom view of the chassis. The connection portions between the first holding faces and the second holding faces form apex portions 94C and 95C. In the grip faces 94 and 95, since the user can rest a part of the fingers F (for example, a first joint) on the apex portions 94C and 95C, it is possible to more stably hold the chassis. In the grip face 95, the first holding face 95A and the second holding face 95B are curved with a predetermined curvature so as to be concave to the rear surface, but the apex portion 95C is formed. Accordingly, the basic shape of the grip face 95 is convex to the rear surface.

Figure 14D:
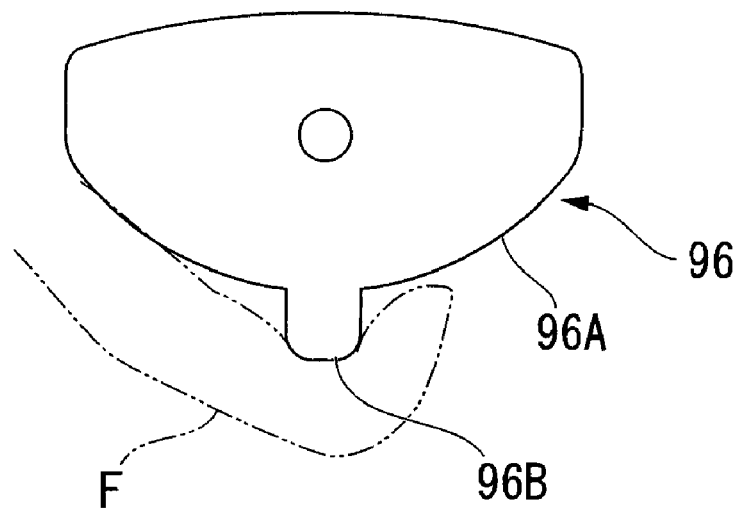
FIG. 14D is a diagram schematically illustrating the shape of a grip face in an endoscopic device according to another modification of the invention.

FIG. 14D shows a grip face 96 including a protrusion 96B protruding from a spherical basic face 96A. In this grip face, the user can rest the first joints of the fingers F on the protrusion 96B, thereby stabilizing the holding.

Figure 14E:
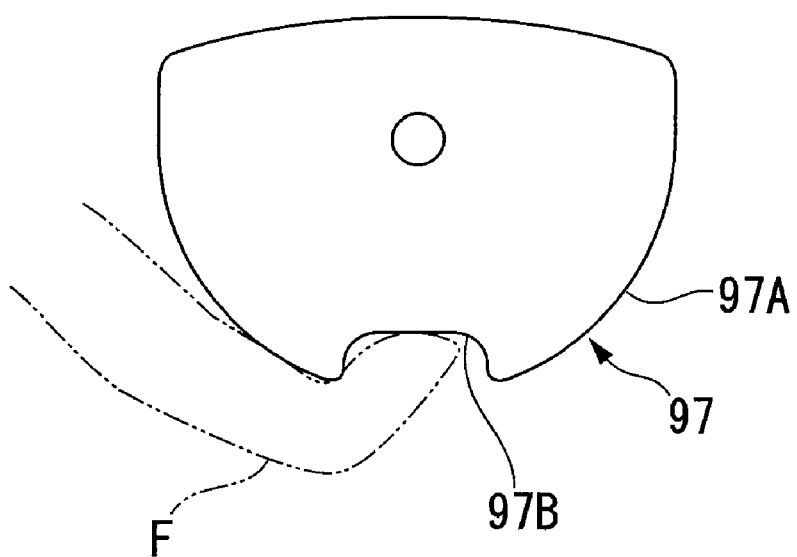
FIG. 14E is a diagram schematically illustrating the shape of a grip face in an endoscopic device according to another modification of the invention.

FIG. 14E shows a grip face 97 including a concave portion 97B in a spherical basic face 97A. In this grip face, the user can stabilize the holding by resting the first joints of the fingers F on the concave portion 97B. Since the concave portion 97B itself is not convex to the rear surface but has the spherical basic face 97A, the basic shape of the grip face 97 is convex to the rear surface.

In this way, the grip face can be appropriately set depending on the usage of the endoscopic device, the users, or the like while having a basic shape convex to the rear surface. The grip face can have a shape convex to the rear surface in at least one of the side view of the chassis and the bottom view of the chassis. Even when the grip face is not convex to the rear surface in both of the side view and the bottom view like the endoscopic device 1, the effect of stabilizing the user's holding can be obtained to a certain extent.

In the above-mentioned embodiment, it has been described that the center of gravity position of the endoscopic device other than the insertion section is set within the region A1 that includes the connection portion between the upper section and the lower section of the chassis and the periphery thereof. However, even when the center of gravity is set to be located out of the region A1 but within the region A3 shown in FIG. 6, the effect of stabilizing the holding and the operation can be obtained to a certain extent.

Although it has been described in the above-mentioned embodiment that the ground-contact members 68 allowing the chassis 61 to self-stand by itself in the inversion mode are disposed in two separated places, the ground-contact member may be disposed in a straight line with a constant length (for example, a length capable of connecting two places in which the ground-contact members 68 are disposed in the embodiment) at the upper peripheral edge of the upper rear surface 64B. In this case, the chassis 61 can be appropriately allowed to self-stand and can be used in the inversion mode.

Although it has been described in the above-mentioned embodiment that the illumination mechanism 12 is disposed at the distal end of the insertion section 10, a light source may be disposed in the chassis and a light guide member such as a light guide may be disposed in the insertion section to supply illumination light to the distal end of the insertion section like some endoscopic devices in the related art.

The invention can be suitably applied to an endoscopic device capable of using only a battery as a power source, but it may be supplied with power from an external power source in addition to the battery. In this case, when the center of gravity position of the endoscopic device other than the insertion section is greatly changed due to the detachment of the battery, a dummy member having the same shape and size as the battery and having a weight smaller than that of the battery and capable of setting the center of gravity position within a predetermined region in the state where it is received in the battery receiver may be provided and may be received in the battery receiver for use at the time of using the external power source.

It has been described in the above-mentioned embodiment that the friction member having elasticity is attached to the first holding face and the second holding face. However, even when a friction member not being elastically deformed is selected and attached to the holding faces so as to raise the friction coefficient, the above-mentioned effect can be obtained to a certain extent.

Although it has been described in the above-mentioned embodiment that the reinforcing member and the self-stand assist member are attached to the base end of the insertion section connected to the chassis, only one of the reinforcing member and the self-stand assist member may be attached, or an endoscopic device may be allowed to self-stand with only the connection portion of the insertion section and the edge portion of the chassis close to the display unit without attaching any of the reinforcing member and the self-stand assist member.

According to the above-mentioned endoscopic device, it is possible to stably hold and operate the chassis.

The invention claimed is:

1. An endoscope comprising:
    a long flexible insert portion which has an imaging device on a tip thereof;
    a display portion which displays an image obtained by the imaging device;
    a manipulation portion for bending the insert portion;
    a casing which houses the display portion and the manipulation portion at a front side, and to which the insert portion is connected at a back side; and
    a battery which supplies electricity to the display portion,
    wherein the casing has an upper portion in which the display portion is housed and a lower portion in which the manipulation portion is housed, wherein the insert portion is connected to the lower portion, is coaxial with the manipulation portion, and extends from the lower portion in a first direction, and wherein a line connecting a center of gravity of the battery and a center of gravity of the casing while the battery is housed in the casing extends in a second direction that intersects the first direction at a position inside the lower portion.

* * * * *